US00PP24298P3

(12) United States Plant Patent
Johnson, Jr. et al.

(10) Patent No.: US PP24,298 P3
(45) Date of Patent: Mar. 11, 2014

(54) BLACKBERRY PLANT NAMED 'HJ-7'

(50) Latin Name: *Rubus ursinus*
Varietal Denomination: HJ-7

(75) Inventors: Harold A. Johnson, Jr., Aromas, CA (US); Judith E. Johnson, Aromas, CA (US)

(73) Assignee: Plant Sciences, Inc., Watsonville, CA (US)

( * ) Notice: Subject to any disclaimer, the term of this patent is extended or adjusted under 35 U.S.C. 154(b) by 173 days.

(21) Appl. No.: 13/385,249

(22) Filed: Feb. 10, 2012

(65) Prior Publication Data

US 2013/0212754 P1 Aug. 15, 2013

(51) Int. Cl.
*A01H 5/00* (2006.01)

(52) U.S. Cl.
USPC ..... Plt./203

(58) Field of Classification Search
USPC ..... Plt./203, 204
See application file for complete search history.

*Primary Examiner* — Kent L Bell
(74) *Attorney, Agent, or Firm* — Foley & Lardner LLP

(57) ABSTRACT

Description and specifications of a new and distinct blackberry which originates from seed produced by a hand pollinated cross of two, non-patented varieties; 'Obsidian' as the female and 'Eaton' as the male. This new, trailing cultivar can be distinguished by it's consistant, large fruit size and appearance during the early spring and summer period for the fresh market. The fruit of this cultivar is produced on red, strong, thorny canes. When plants are grown and pruned correctly, yield in Central California, USA can be up to 4,500 crates/ac if the fruit is handled and shipped correctly.

2 Drawing Sheets

Figure 1:
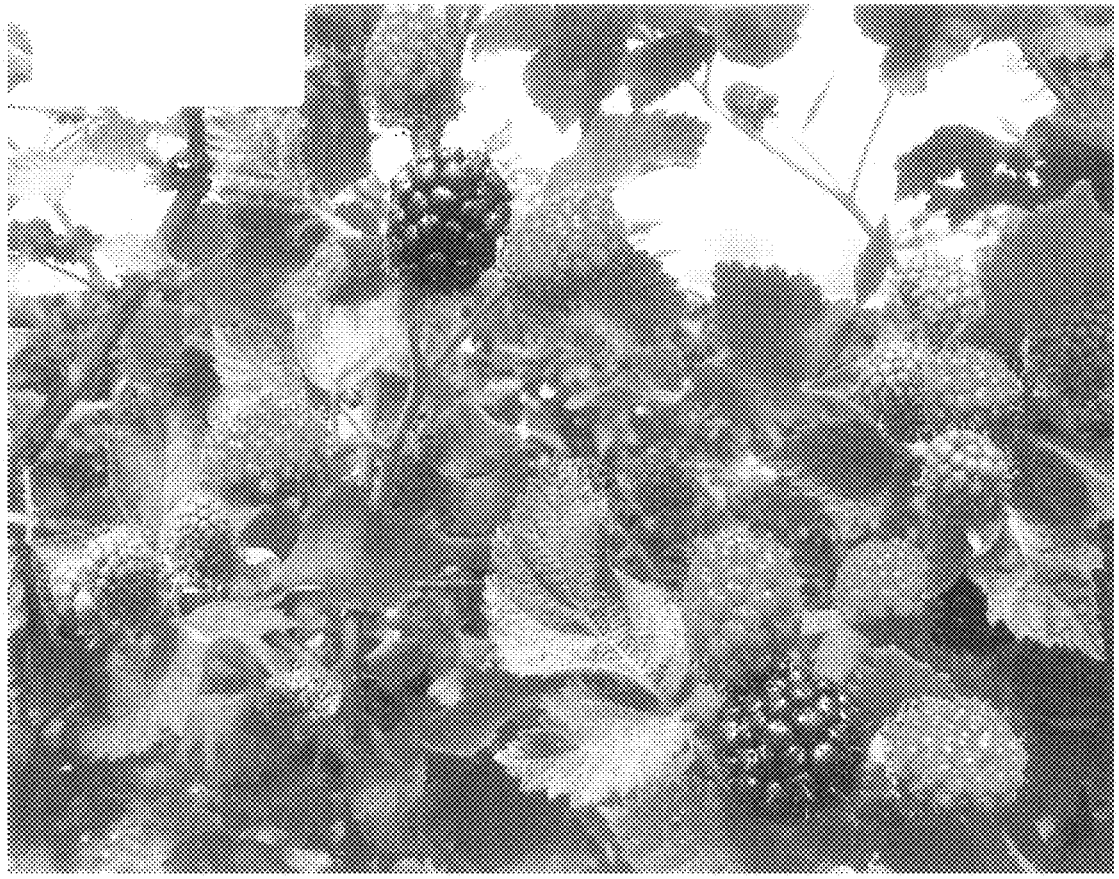

Latin name of the genus and species of the plant claimed: *Rubus ursinus.*

Variety denomination: 'HJ-7'.

BACKGROUND OF THE INVENTION

The present invention relates to a new and distinct trailing blackberry variety designated as 'HJ-7'. This new variety is a result of a controlled cross made by the inventors, Harold A. Johnson Jr. and Judith E. Johnson, in 2005 between the blackberry variety designated 'Obsidian' (female) and the blackberry variety designated 'Eaton' (male), both parental varieties unpatented. The variety 'HJ-7' is botanically known as *Rubus ursinus.*

The seedling resulting from the aforementioned cross was selected from a controlled breeding plot near Watsonville, Santa Cruz County, Calif. in 2007 by the inventors. After its selection, the new variety was further asexually propagated beginning in October of 2007 in Watsonville, Santa Cruz County, Calif. by tissue culture. The new variety was then tested in fruiting fields in Santa Cruz County, Calif. This propagation has demonstrated that the combination of traits disclosed herein as characterizing the new variety are fixed and remain true to type through successive generations of asexual reproduction.

SUMMARY OF THE INVENTION

'HJ-7' is primarily adapted to the climate and growing conditions of the Santa Cruz and Monterey Counties in Calif., and is being tested in Southern California, and in Europe. 'HJ-7' has reacted favorably to the coastal climates of northern coastal California, but for maximum fruit production, 'HJ-7' requires consistent soil moisture and adequate nutrition. 'HJ-7' reacts favorably to an environment created by plastic tunnels.

The following traits have been observed and are determined to be unique characteristics of 'HJ-7', which in combination distinguish this blackberry plant as a new and distinct variety.

1. consistent early spring production of large size, good quality fruit.
2. Medium to large fruit size responds favorably to careful packing when shipped in 6 oz. clamshell baskets;
3. thorny and trailing plant structure; and
4. Early spring fruit production, starting in May, with peak production in early June, and continued, limited production through June and further, when grown in Santa Cruz County, Calif.

When the new blackberry variety 'HJ-7' is compared to the female parental variety 'Obsidian', the following trait differences have been observed:

1. The peak fruit production of 'HJ-7' occurs slightly earlier than 'Obsidian', and earlier than most trailing and erect types;
2. in holding testing after picking, the average flavor rating was the same, but 'HJ-7' rated higher in appearance than 'Obsidian' after various days in cold storage;
3. 'HJ-7' has produced less crates per acre than 'Obsidian'.
4. the average soluble solids concentration of 'Obsidian' is 10.8, and 'HJ-7' is 12.0.
5. the average seed size of 'HJ-7' is is 3.82 mm in length and 2.33 mm in width, and 'Obsidian' 4.00 mm in length and 1.93 mm in width.

When the new blackberry variety 'HJ-7' is compared to the male parental variety 'Eaton', the following trait differences have been observed:

1. 'HJ-7' has thorns whereas 'Eaton' has no thorns;
2. the fruit size and shape of 'HJ-7' is medium, and ovate to elliptical while the fruit size and shape of 'Eaton' is small, and long conic;

3. 'HJ-7' has determinate inflorescence which limits the number of peduncles as well as the length and number of each pedicel per plant leading to a limited number of berries which are larger in size, whereas 'Eaton' has indeterminate inflorescence which produces a larger number of smaller berries per plant;
4. 'HJ-7' has an abundant supply of pollen which leads to a minimum number of malformed fruit, whereas 'Eaton' lacks consistently good pollen at the end of its indeterminate inflorescences and thus often produces poorly-shaped, small fruit;
5. 'HJ-7' has larger leaves than 'Eaton'; and
6. 'HJ-7' has stronger overall vegetative strength than 'Eaton'.

When the new blackberry variety 'HJ-7' is compared to the similar variety 'HJ-6', the following trait differences have been observed:

1. the fruit production of 'HJ-6' occurs later in the season than 'HJ-7';
2. the overall (total season) production of 'HJ-6' is greater than that of 'HJ-7';
3. the average berry size of 'HJ-6' (8-10 g) is larger than the average berry size of 'HJ-7' (6-7 g);
4. the leaf color of 'HJ-6' is lighter in early June (7.5 GY4-4) than the leaf color of 'HJ-7' at the same point in the season (7.5 GY3-2); and
5. 'HJ-6' is considered superior to 'HJ-7' in side-by-side flavor test results.

BRIEF DESCRIPTIONS OF THE PHOTOGRAPHS

The accompanying color photographs illustrate the overall appearance of typical specimens of the new blackberry variety, 'HJ-7' as true as reasonably possible with color reproductions of this type. Plants shown in the photographs are two years old.

FIG. 1, taken May 18, 2009 illustrates typical early fruit during May showing large, circular berries with large drupelets. This is in contrast to subsequent fruit production which becomes medium ovate in outline. FIG. 1 also illustrates floricanes at two stages of maturity; the darker cane being the more mature. The pedicels and peduncles both have thorns; some pointed outward and some downward. The leaflets have bi-serrate serrations and are ovate with an acuminate to acute apex.

Figure 2:
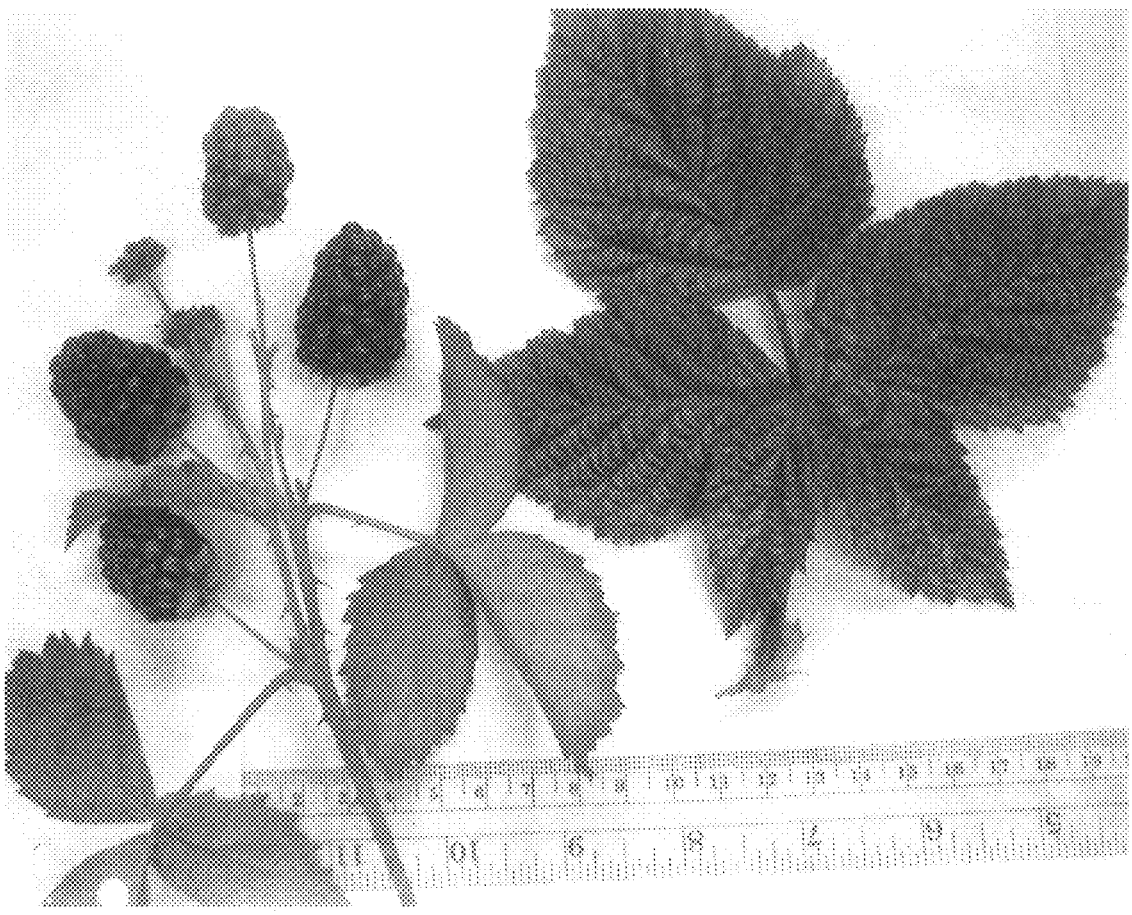

FIG. 2, taken in October 2009, illustrates the typical large fruit produced by 'HJ-7' that is long-conical to oblong in shape, contains large droplets, and is present in all by the early season crop. There are thorns on some pedicels. FIG. 2 further illustrates the typical foliage produced by 'HJ-7'; that comprises mostly 5 leaflets, each leaflet being ovate in shape, with an acuminate to acute apex, bi-serrate serrations, and palmate venation. The leaf petiole, as well as, the fruit peduncle, as further illustrated in FIG. 2, has a red surface.

DETAILED BOTANICAL DESCRIPTION

The following description of 'HJ-7' unless otherwise noted, is based on observations taken during the 2008 and 2009 growing seasons in Santa Cruz County, Calif. The plants observed were two years old. The phenotypical descriptions and color designations stated for the new variety may vary, depending upon variations in environmental factors, including weather (temperature, humidity and light intensity), day length, soil type, location and cultural conditions. 'HJ-7' has not been observed under all possible environmental conditions.

Table 1 provides a botanical comparison of 'HJ-7' to the following two (2) unpatented, commercially grown varieties in Santa Cruz County, Calif.: (1) 'Obsidian', a trailing, semi-erect, thorny and early ripening variety (female parental variety, unpatented), and (2) 'HJ-6' (U.S. Plant Pat. No. 23,270), a sibling to 'HJ-7'.

TABLE 1

| CHARACTERISTIC | Comparison Variety 1 'HJ-6' (U.S. Plant Pat. No. 23,270) | Comparison Variety 2 OBSIDIAN (unpatented) | New Variety 'HJ-7' |
|---|---|---|---|
| Plant Form | | | |
| Growth Habit | Trailing, semi-upright | Trailing, semi-upright | Trailing-semi-upright |
| Plant Height | 4 to 5 feet | 4 to 5 feet | 4 to 5 feet |
| Suckering | Abundant | Abundant | Abundant |
| Branching | Indeterminate | Indeterminant | Indeterminate |
| Cane Texture | Thorny | Thorny | Thorny |
| Hardiness | Very Hardy | Very Hardy | Very Hardy |
| Canes | hair on new growth | Hair on new growth | hair on new growth |
| Diameter-Primocane | Large-1.8 cm | Medium-1.2 cm | Med to Large 1.2-2.0 cm |
| Floricane | Same Diameter | Same Diameter | Same Diameter |
| Immature Primocane | Round to Angular | Round to Angular | Round to Angular |
| Mature Primocane | | | |
| Internode Length | | | |
| Color | | | |
| Prickles | Red to green | Red to Green | Red to Green |
| Mature Canes | All red 2.5R 2/2 | Upper side red 2.5R 2/6 | Upper side red 2.5R2/6 |
| Foliage | Robust, large leaves | Robust, medium leaves | Robust, medium leaves |
| Predominate Number of Leaflets | Mostly 5; some 3 | Mostly 3, some 4, 5 | Mostly 3, some 5 |
| Leaf Type | Mainly palmate | Odd palmate to intermediate | Mainly palmate |
| Leaf Color | | | |
| Upper Surface | 5 GY 3/4 | 5 GY 3/4 | 5GY 3/2 |
| Lower Surface | 7.5 GY 5/6 | 7.5 GY 5/6 | 7.5 GY6/6 |
| Central Leaflet Shape | Ovate with acuminate apex | Ovate with acute to acuminate apex | Ovate with acuminate apex |
| Leaflet Relief Between Veins | Medium | Strong | Strong |
| Spine Attitude | Outward, some down | Mainly outward | Outward and many down |
| Serrations of Leaflets | Shallow | Shallow | Shallow |
| Leaf Incision of Margin | Bi-serrate | Bi-serrate | Bi-serrate |
| Pubescence | Infrequent, no glandular hairs | Abundant, no glandular hairs | Infrequent, no glandular hairs |
| Petioles Width | 2.41 mm | 1.5-2.0 mm | 1.5-2.0 mm |
| Color | Top-2.5R2/2; Bottom 5GY2/2 | Predom 5GY 2/2 | Predom5GY 2/2 |
| Texture | Smooth w small thorns | Predom smooth | Smooth |
| Length | 4-6 cm | 3-5 cm | 2-3 cm |
| Flowers | | | |
| Blooming Period | Mid March-April | Early March-April | Early March-April |
| Color | | | |
| Pedicels | Short Pedicels 3-6 cm | Medium 3-6 cm | Medium 3-6 cm |

TABLE 1-continued

| CHARACTERISTIC | Comparison Variety 1 'HJ-6' (U.S. Plant Pat. No. 23,270) | Comparison Variety 2 OBSIDIAN (unpatented) | New Variety 'HJ-7' |
|---|---|---|---|
| Size of Florets | | | |
| Petals | | | |
| Number | 5 to 6 | 5 | 5 |
| Shape | Irregular elliptical | Irregular elliptical | Irregular elliptical |
| Color | WhiteN9.25/ 84.2% R | White N9.25/ 84.2% R | White N9.25/ 84.2% R |
| Pollen | Strong | Strong | Strong |
| # of Sepals | 5-; Length 5 to 10 mm in length; some sepal with leaf extensions | 5; Length 4 to 8 mm. Some sepals with leaf extensions | 5; Length 4 to 6 mm. Rare leaf extensions on sepals |
| #of Pistils | | | |
| Fruit | | | |
| Productivity | Medium--high; long picking season | High | Medium |
| Time of Fruiting | Late spring to summer, June-July | Late May to July | May to July |
| Size | Very large; avg 8 gm | Medium-large; avg 6 gm | Medium-large; avg 6-8 gm |
| Shape | Oblong to conic | Elliptical, some circular | Oblong to conic; some elliptical in early season |
| Color | | | |
| Immature | Green to red | Green to red | Green to red |
| Mature | N1.75/2.5% R | N1.75/2.5R | N1.75/2.5% R |
| Glossiness | Medium to full | Medium to full | Medium to Full |

TABLE 1-continued

| CHARACTERISTIC | Comparison Variety 1 'HJ-6' (U.S. Plant Pat. No. 23,270) | Comparison Variety 2 OBSIDIAN (unpatented) | New Variety 'HJ-7' |
|---|---|---|---|
| Weight | 6 to 12 gm | 6 to 8 gm | 6 to 10 gm |
| Length | 30 to 35 mm | 25 to 30 mm | 25 to 30 mm |
| Diameter | 20 to 25 mm | 20 to 25 mm | 20 to 30 mm |
| Drupelets | | | |
| Size | 3 to 4 mm | 4.0 to 5.0 mm | 3 to 4.5 mm |
| # per Berry | | | |
| Seed | | | |
| Size | Length 3.54 mm; Width 1.93 mm | Length 4.00 mm Width 1.93 mm | Length 3.82; Width 2.33 mm |
| Weight | | | |
| Soluble Solids | 9.2% | 10.8% | 12.0% |
| pH | | | |
| Yield Ave of 2 yrs | 6991 crates/acre | 5408 crates/acre avg. | 3842 crates/ac |
| Disease/Pest Resistance | Red Mite susceptible | Red Mite susceptible | Red Mite susceptible |
| Uses | Fresh Market | Fresh Market; Processing | Fresh Market |

When color is identified, the Munsell Book of Color (March 1976) is used.
Yield-crates/acre (crate = 4.5 lb)

What is claimed is:

1. A new and distinct variety of *Rubus ursinus* plant named 'HJ-7', as herein described and illustrated by the characteristics set forth above.

* * * * *